(12) United States Patent
Ferrari et al.

(10) Patent No.: US 9,250,214 B2
(45) Date of Patent: Feb. 2, 2016

(54) CMM WITH FLAW DETECTION SYSTEM

(71) Applicant: Hexagon Metrology, Inc., North Kingstown, RI (US)

(72) Inventors: Paul Ferrari, Carlsbad, CA (US); Hyun Kwon Jung, Oceanside, CA (US); Hogar Tait, Carlsbad, CA (US)

(73) Assignee: Hexagon Metrology, Inc., North Kingstown, RI (US)

( * ) Notice: Subject to any disclaimer, the term of this patent is extended or adjusted under 35 U.S.C. 154(b) by 375 days.

(21) Appl. No.: 13/797,537

(22) Filed: Mar. 12, 2013

(65) Prior Publication Data

US 2014/0260627 A1   Sep. 18, 2014

(51) Int. Cl.
*G01N 29/265* (2006.01)
*G01B 21/04* (2006.01)
*G01N 29/04* (2006.01)
*G01N 29/22* (2006.01)

(52) U.S. Cl.
CPC .............. *G01N 29/265* (2013.01); *G01B 21/04* (2013.01); *G01B 21/042* (2013.01); *G01N 29/043* (2013.01); *G01N 29/225* (2013.01)

(58) Field of Classification Search
CPC . G01N 29/265; G01N 29/225; G01N 29/043; G01B 21/042; G01B 21/04
USPC .......................................................... 73/618
See application file for complete search history.

(56) References Cited

U.S. PATENT DOCUMENTS

| | | |
|---|---|---|
| 4,212,072 A | 7/1980 | Huelsman et al. |
| 4,332,171 A | 6/1982 | Lida et al. |
| 4,431,007 A | 2/1984 | Amazeen et al. |
| 4,492,036 A | 1/1985 | Beckwith |
| 4,492,119 A | 1/1985 | Dulapa et al. |
| 4,972,090 A | 11/1990 | Eaton |
| 5,078,145 A | 1/1992 | Furuhata |
| 5,084,981 A | 2/1992 | McMurtry et al. |
| 5,088,337 A | 2/1992 | Bennett |
| 5,148,377 A | 9/1992 | McDonald |
| 5,187,874 A | 2/1993 | Takahashi et al. |
| 5,189,797 A | 3/1993 | Granger |
| 5,251,156 A | 10/1993 | Heier et al. |
| 5,396,712 A | 3/1995 | Herzog |
| 5,408,754 A | 4/1995 | Raab |
| 5,412,880 A | 5/1995 | Raab |
| 5,488,952 A | 2/1996 | Schoolman |
| 5,505,003 A | 4/1996 | Evans et al. |
| 5,510,977 A | 4/1996 | Raab |
| 5,521,847 A | 5/1996 | Ostrowski et al. |
| 5,526,576 A | 6/1996 | Fuchs et al. |

(Continued)

FOREIGN PATENT DOCUMENTS

| | | |
|---|---|---|
| DE | 4345091 | 7/1995 |
| DE | 10112977 | 11/2002 |

(Continued)

*Primary Examiner* — J M Saint Surin

(74) *Attorney, Agent, or Firm* — Knobbe Martens Olson & Bear LLP

(57) ABSTRACT

A flaw detection system includes a CMM having a base and one or more transfer members, one or more articulation members connecting the one or more transfer members to the base, and a flaw detection sensor at a distal end, the CMM being configured to measure a location of the flaw detection sensor, and a processor configured to correlate the location of the flaw detection sensor as measured by the CMM with data detected by the flaw detection sensor.

22 Claims, 14 Drawing Sheets

(56) References Cited

U.S. PATENT DOCUMENTS

| | | | |
|---|---|---|---|
| 5,528,505 A | 6/1996 | Granger et al. | |
| 5,611,147 A | 3/1997 | Raab | |
| 5,615,489 A | 4/1997 | Breyer et al. | |
| 5,748,767 A | 5/1998 | Raab | |
| 5,757,499 A | 5/1998 | Eaton | |
| 5,768,792 A | 6/1998 | Raab | |
| 5,794,356 A | 8/1998 | Raab | |
| 5,822,450 A | 10/1998 | Arakawa et al. | |
| 5,829,148 A | 11/1998 | Eaton | |
| 5,867,916 A * | 2/1999 | Matzkovits | 33/503 |
| 5,978,748 A | 11/1999 | Raab | |
| 5,991,704 A | 11/1999 | Rekar et al. | |
| 6,134,506 A | 10/2000 | Rosenberg et al. | |
| 6,151,789 A | 11/2000 | Raab et al. | |
| 6,161,079 A | 12/2000 | Zink et al. | |
| 6,163,973 A * | 12/2000 | Matsumiya et al. | 33/559 |
| 6,166,811 A | 12/2000 | Long et al. | |
| 6,219,928 B1 | 4/2001 | Raab et al. | |
| 6,366,831 B1 | 4/2002 | Raab | |
| 6,413,212 B1 | 7/2002 | Raab | |
| 6,425,865 B1 | 7/2002 | Salcudean et al. | |
| 6,430,828 B1 | 8/2002 | Ulbrich | |
| 6,487,896 B1 | 12/2002 | Dall'Aglio | |
| 6,526,670 B1 | 3/2003 | Carli | |
| 6,598,306 B2 | 7/2003 | Eaton | |
| 6,604,404 B2 | 8/2003 | Paltieli et al. | |
| 6,611,346 B2 | 8/2003 | Granger | |
| 6,611,617 B1 | 8/2003 | Crampton | |
| 6,618,496 B1 | 9/2003 | Tassakos et al. | |
| 6,668,466 B1 | 12/2003 | Bieg et al. | |
| 6,759,648 B2 | 7/2004 | Baxter et al. | |
| 6,817,108 B2 | 11/2004 | Eaton | |
| 6,892,465 B2 | 5/2005 | Raab et al. | |
| 6,904,691 B2 | 6/2005 | Raab et al. | |
| 6,925,722 B2 | 8/2005 | Raab et al. | |
| 6,931,745 B2 | 8/2005 | Granger | |
| 6,952,882 B2 | 10/2005 | Raab et al. | |
| 6,984,236 B2 | 1/2006 | Raab | |
| 6,988,322 B2 | 1/2006 | Raab et al. | |
| 7,003,892 B2 | 2/2006 | Eaton et al. | |
| 7,017,275 B2 | 3/2006 | Raab et al. | |
| 7,043,847 B2 | 5/2006 | Raab et al. | |
| 7,051,450 B2 | 5/2006 | Raab et al. | |
| 7,069,664 B2 | 7/2006 | Raab et al. | |
| 7,073,271 B2 | 7/2006 | Raab et al. | |
| 7,096,077 B2 | 8/2006 | Price et al. | |
| 7,152,456 B2 | 12/2006 | Eaton | |
| 7,174,651 B2 | 2/2007 | Raab et al. | |
| 7,227,647 B2 * | 6/2007 | Ferger | 356/600 |
| 7,269,910 B2 | 9/2007 | Raab et al. | |
| 7,296,364 B2 | 11/2007 | Seitz et al. | |
| 7,296,979 B2 | 11/2007 | Raab et al. | |
| 7,313,264 B2 | 12/2007 | Crampton | |
| 7,372,581 B2 | 5/2008 | Raab et al. | |
| 7,395,606 B2 | 7/2008 | Crampton | |
| 7,441,341 B2 | 10/2008 | Eaton | |
| 7,525,276 B2 | 4/2009 | Eaton | |
| 7,546,689 B2 | 6/2009 | Ferrari et al. | |
| 7,568,293 B2 | 8/2009 | Ferrari | |
| 7,578,069 B2 | 8/2009 | Eaton | |
| D599,226 S | 9/2009 | Gerent et al. | |
| 7,624,510 B2 | 12/2009 | Ferrari | |
| 7,640,674 B2 | 1/2010 | Ferrari et al. | |
| 7,676,945 B2 | 3/2010 | Prestidge et al. | |
| 7,693,325 B2 | 4/2010 | Pulla et al. | |
| 7,731,662 B2 | 6/2010 | Anderson et al. | |
| 7,743,524 B2 | 6/2010 | Eaton et al. | |
| 7,774,949 B2 | 8/2010 | Ferrari | |
| 7,779,548 B2 | 8/2010 | Ferrari | |
| 7,784,194 B2 | 8/2010 | Raab et al. | |
| 7,805,854 B2 | 10/2010 | Eaton | |
| 7,908,757 B2 | 3/2011 | Ferrari | |
| 7,984,558 B2 | 7/2011 | Ferrari | |
| D643,319 S | 8/2011 | Ferrari et al. | |
| 7,993,289 B2 | 8/2011 | Quistgaard et al. | |
| 8,001,697 B2 | 8/2011 | Danielson et al. | |
| 8,015,721 B2 | 9/2011 | Eaton et al. | |
| 8,020,308 B2 * | 9/2011 | Lee et al. | 33/503 |
| 8,082,673 B2 | 12/2011 | Desforges et al. | |
| 8,099,877 B2 | 1/2012 | Champ | |
| 8,104,189 B2 | 1/2012 | Tait | |
| 8,112,896 B2 | 2/2012 | Ferrari et al. | |
| 8,122,610 B2 | 2/2012 | Tait et al. | |
| 8,123,350 B2 | 2/2012 | Cannell et al. | |
| 8,127,458 B1 | 3/2012 | Ferrari | |
| 8,145,446 B2 | 3/2012 | Atwell et al. | |
| 8,151,477 B2 | 4/2012 | Tait | |
| 8,176,646 B2 | 5/2012 | Ferrari | |
| 8,201,341 B2 | 6/2012 | Ferrari | |
| 8,220,173 B2 | 7/2012 | Tait | |
| 8,229,208 B2 | 7/2012 | Pulla et al. | |
| 8,250,772 B2 * | 8/2012 | Eaton | 33/503 |
| 8,272,603 B2 | 9/2012 | Fadler et al. | |
| 8,327,555 B2 | 12/2012 | Champ | |
| 8,336,220 B2 | 12/2012 | Eaton et al. | |
| 8,402,669 B2 | 3/2013 | Ferrari et al. | |
| 2002/0128790 A1 * | 9/2002 | Woodmansee | 702/81 |
| 2005/0193451 A1 | 9/2005 | Quistgaard et al. | |
| 2005/0276466 A1 * | 12/2005 | Vaccaro et al. | 382/152 |
| 2007/0073149 A1 | 3/2007 | Kelly et al. | |
| 2007/0276250 A1 | 11/2007 | Donaldson | |
| 2008/0016711 A1 | 1/2008 | Baebler | |
| 2009/0088639 A1 | 4/2009 | Maschke | |
| 2009/0165317 A1 | 7/2009 | Little | |
| 2010/0205816 A1 | 8/2010 | Wu et al. | |
| 2010/0298712 A1 | 11/2010 | Pelissier et al. | |
| 2011/0112786 A1 | 5/2011 | Desforges et al. | |
| 2011/0175745 A1 | 7/2011 | Atwell et al. | |
| 2011/0213247 A1 | 9/2011 | Shammas | |

FOREIGN PATENT DOCUMENTS

| | | |
|---|---|---|
| DE | 20 2008 007 949 U1 | 2/2008 |
| EP | 0522610 | 1/1993 |
| EP | 2 249 153 A1 | 11/2010 |
| FR | 2740546 | 4/1997 |
| GB | 2274526 | 7/1994 |
| JP | 05/031685 | 2/1993 |
| JP | 2003/021133 | 1/2003 |
| JP | 2003/175484 | 6/2003 |
| WO | WO 98/08050 | 2/1998 |

* cited by examiner

CMM WITH FLAW DETECTION SYSTEM

BACKGROUND OF THE INVENTION

1. Field of the Invention

The present invention relates to articulated arms and coordinate measurement, and more particularly to coordinate measurement machines incorporating ultrasonic flaw detection.

2. Description of the Related Art

Rectilinear measuring systems, also referred to as coordinate measuring machines (CMMs) and articulated arm measuring machines, are used to generate highly accurate geometry information. In general, these instruments capture the structural characteristics of an object for use in quality control, electronic rendering and/or duplication. One example of a conventional apparatus used for coordinate data acquisition is a portable coordinate measuring machine (PCMM), which is a portable device capable of taking highly accurate measurements within a measuring sphere of the device. Such devices often include a probe mounted on an end of an arm that includes a plurality of transfer members connected together by joints. The end of the arm opposite the probe is typically coupled to a moveable base. Typically, the joints are broken down into singular rotational degrees of freedom, each of which is measured using a dedicated rotational transducer. During a measurement, the probe of the arm is moved manually by an operator to various points in the measurement sphere. At each point, the position of each of the joints must be determined at a given instant in time. Accordingly, each transducer outputs an electrical signal that varies according to the movement of the joint in that degree of freedom. Typically, the probe also generates a signal. These position signals and the probe signal are transferred through the arm to a recorder/analyzer. The position signals are then used to determine the position of the probe within the measurement sphere. See e.g., U.S. Pat. Nos. 5,829,148 and 7,174,651, which are incorporated herein by reference in their entireties.

Generally, there is a demand for a CMM with a high degree of accuracy, high reliability and durability, substantial ease of use, low cost, and ultrasonic flaw detection capability, among other qualities. The disclosure herein provides improvements of at least some of these qualities.

SUMMARY OF THE INVENTIONS

In one embodiment, an articulated arm CMM includes an ultrasonic flaw detection system capable of detecting flaws beneath the surface of the selected object.

In another embodiment, an articulated arm CMM includes an ultrasonic flaw detection system incorporating a feature pack providing a portion of the functionality of the ultrasonic flaw detection system.

In another embodiment, an articulated arm CMM includes an ultrasonic flaw detection system providing the capability to overlay flaws on a display with coordinate measurement data.

In another embodiment, an articulated arm CMM includes an ultrasonic flaw detection system providing the capability to incorporate flaws into a three dimensional model of a selected object.

In another embodiment, a flaw detection system includes a CMM having a base and one or more transfer members, one or more articulation members connecting the one or more transfer members to the base, and a flaw detection sensor at a distal end, the CMM being configured to measure a location of the flaw detection sensor, and a processor configured to correlate the location of the flaw detection sensor as measured by the CMM with data detected by the flaw detection sensor.

In another embodiment, a method of sensing flaw in an object includes positioning flaw sensor positioned on a CMM against an object, sensing a characteristic of the object with the flaw sensor, measuring the position of the flaw sensor with the CM, and correlating the position of the flaw sensor with the sensed characteristic of the object.

In another embodiment, a method of sensing flaw in an object includes positioning flaw sensor positioned on a CMM against the object at a plurality of positions, sensing a characteristic of the object with the flaw sensor at each of the plurality of positions, measuring the position of the flaw sensor with the CMM at the plurality of positions where characteristic of the flaw sensor is being sensed, and correlating the positions of the flaw sensor with the sensed characteristics at the plurality of positions.

In another embodiment, a method of measuring data with a CMM includes moving a probe of the CMM to a first probe position; measuring a surface position on an object with a probe; and measuring a flaw point below the surface position with the CMM.

In another embodiment, a method of measuring data with a CMM including moving a probe of the CMM to a plurality of surface positions on an object measuring the plurality of surface positions, and measuring a flaw point below each of the plurality of surface positions with the CMM.

In another embodiment, a method of measuring data with a CMM includes moving a probe of the CMM to a plurality of surface positions on an object measuring the plurality of surface positions, and measuring a flaw start point, a flaw end point and a rear surface of the object below each of the surface positions with the probe of the CMM at the first probe position.

In another embodiment, a method of measuring data with a CMM includes moving a non-contact laser scanner of the CMM to a first probe position, measuring a surface position on an object with a laser scanner, and measuring a flaw point below the surface position with the CMM.

BRIEF DESCRIPTION OF THE DRAWINGS

Further objects, features and advantages of the invention will become apparent from the following detailed description taken in conjunction with the accompanying figures showing illustrative embodiments of the invention, in which.

DETAILED DESCRIPTION OF THE PREFERRED EMBODIMENTS

Further description of certain embodiments of a coordinate acquisition member that can be used with the embodiments described herein can be found in U.S. Pat. No. 8,151,477, filed 26 Mar. 2010, and entitled CMM WITH MODULAR FUNCTIONALITY, which is incorporated by reference herein in its entirety.

Figure 1:
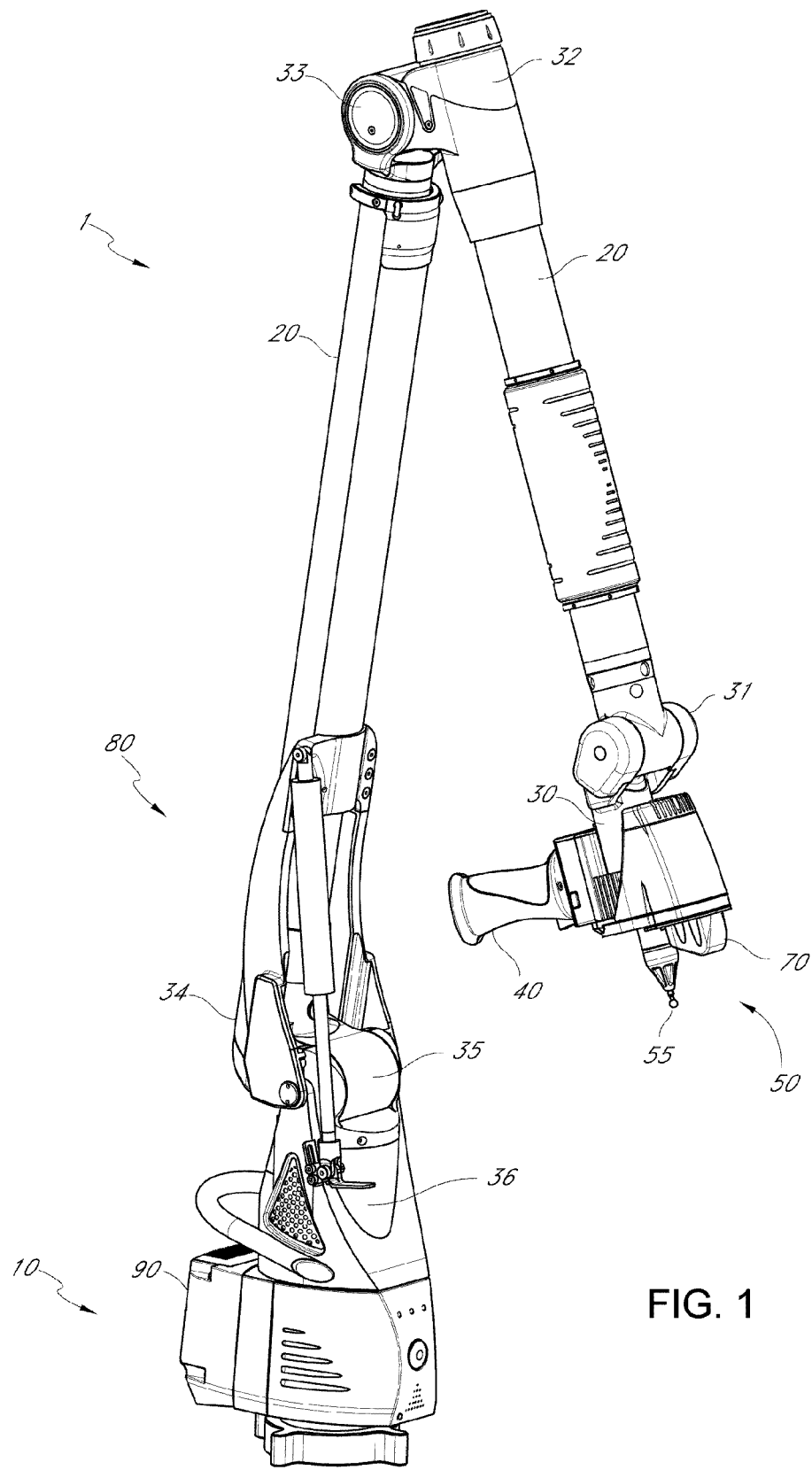
FIG. 1 is a perspective view of an articulated arm.
Figure 1A:
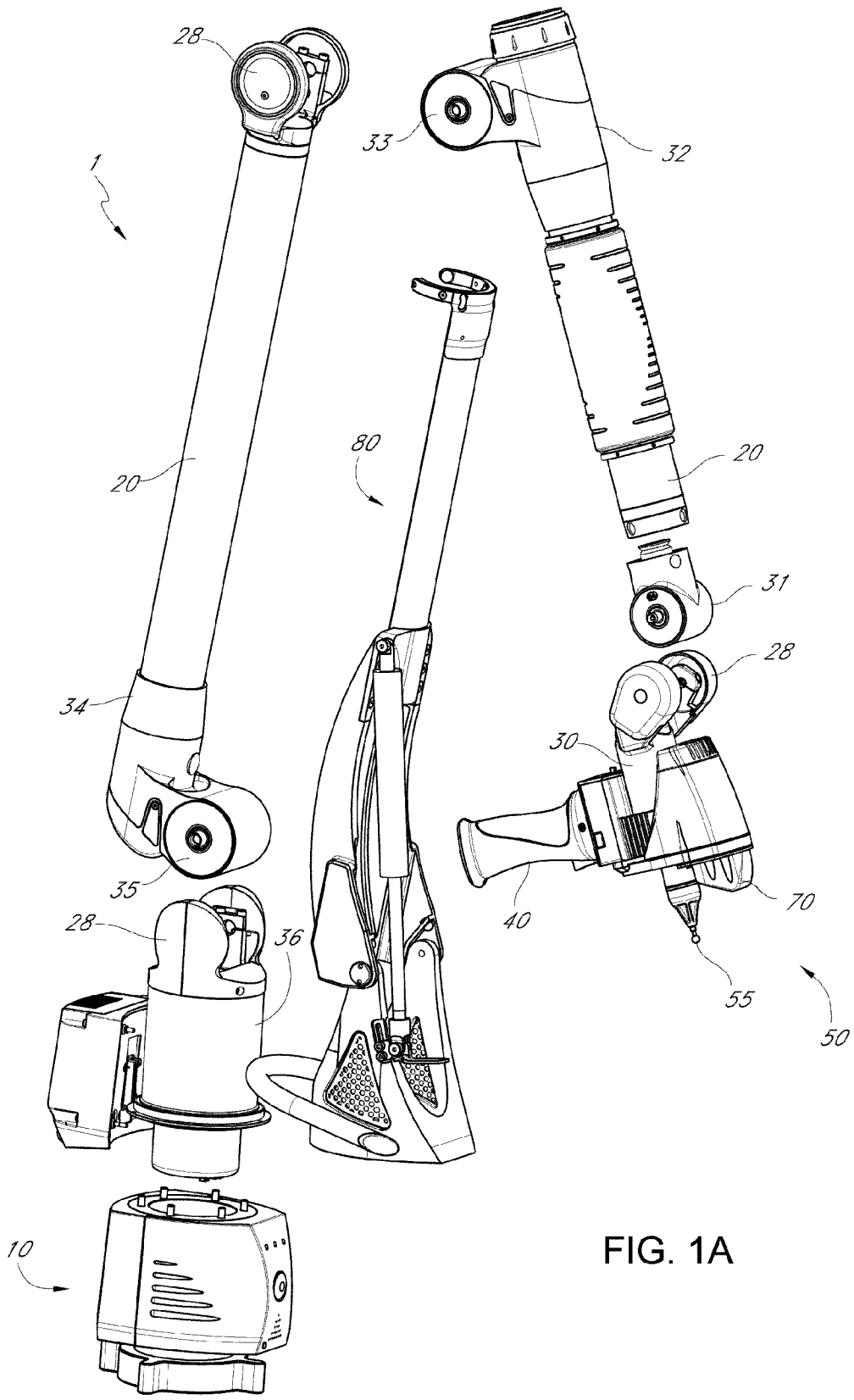
FIG. 1A is an exploded view of the articulated arm of FIG. 1.

FIGS. 1 and 1A illustrate one embodiment of a portable coordinate measuring machine (PCMM) 1 in accordance with the present invention. In the illustrated embodiment, the PCMM 1 can include a base 10, a plurality of rigid transfer members 20, a coordinate acquisition member 50 and a plurality of articulation members 30-36 that form "joint assemblies" connecting the rigid transfer members 20 to one another. The articulation members 30-36 along with the transfer members 20 and hinges (described below) are configured to impart one or more rotational and/or angular degrees of freedom. Through the various members 30-36, 20, the PCMM 1 can be aligned in various spatial orientations thereby allowing fine positioning and orientating of the coordinate acquisition member 50 in three dimensional space.

The position of the rigid transfer members 20 and the coordinate acquisition member 50 may be adjusted using manual, robotic, semi-robotic and/or any other adjustment method. In one embodiment, the PCMM 1, through the various articulation members 30-36, is provided with seven rotary axes of movement. It will be appreciated, however, that there is no strict limitation to the number of axes of movement that may be used, and fewer or additional axes of movement may be incorporated into the PCMM design.

In the embodiment PCMM 1 illustrated in FIG. 1, the articulation members 30-36 can be divided into two functional groupings based on their associated motion members operation, namely: 1) those articulation members 30, 32, 34, 36 which are associated with the swiveling motion associated with a specific and distinct transfer member (hereinafter, "swiveling joints"), and 2) those articulation members 31, 33, 35 which allow a change in the relative angle formed between two adjacent members or between the coordinate acquisition member 30 and its adjacent member (hereinafter, "hinge joints" or "hinges"). While the illustrated embodiment includes four swiveling joints and three hinge joints positioned as to create seven axes of movement, it is contemplated that in other embodiments, the number of and location of hinge joints and swiveling joints can be varied to achieve different movement characteristics in a PCMM. For example, a substantially similar device with six axes of movement could simply lack the swivel joint 30 between the coordinate acquisition member 50 and the adjacent articulation member 20. In still other embodiments, the swiveling joints and hinge joints can be combined and/or used in different combinations.

As is known in the art (see e.g., U.S. Pat. No. 5,829,148, which is hereby incorporated by reference herein) and depicted in FIG. 2D, the transfer members 20 can include a pair of dual concentric tubular structures having an inner tubular shaft 20a rotatably mounted coaxially within an outer tubular sheath 20b through a first bearing mounted proximately to a first end of the member adjacent and a second bearing located at an opposite end of the member and which can be positioned within the dual axis housing 100. The transfer members 20 operate to transfer motion from one end of the transfer member to the other end of the transfer member. The transfer members 20 are, in turn, connected together with articulation members 30-36 to form joint assemblies.

The hinge joint, in turn, is formed, in part, by the combination of a yoke 28 extending from one end of a transfer member (see FIG. 1A), the rotational shaft extending through the articulation members 31, 33, 35 and the articulation members 31, 33, 35 themselves, which rotate about the rotational shaft to form a hinge or hinge joint.

Figure 2:
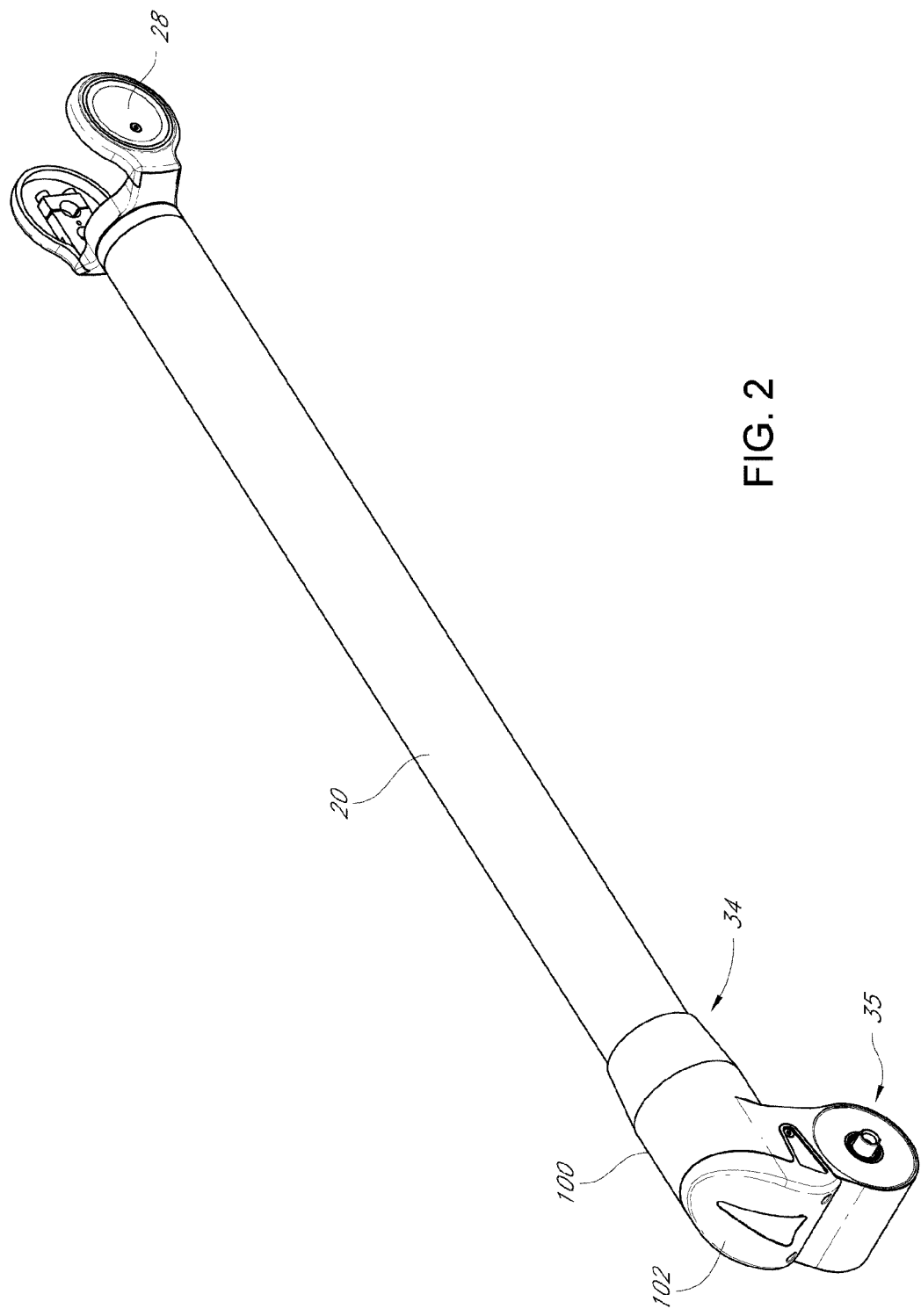
FIG. 2 is a perspective view of a transfer member of the articulated arm of FIG. 1 with its associated articulation members.
Figure 2A:
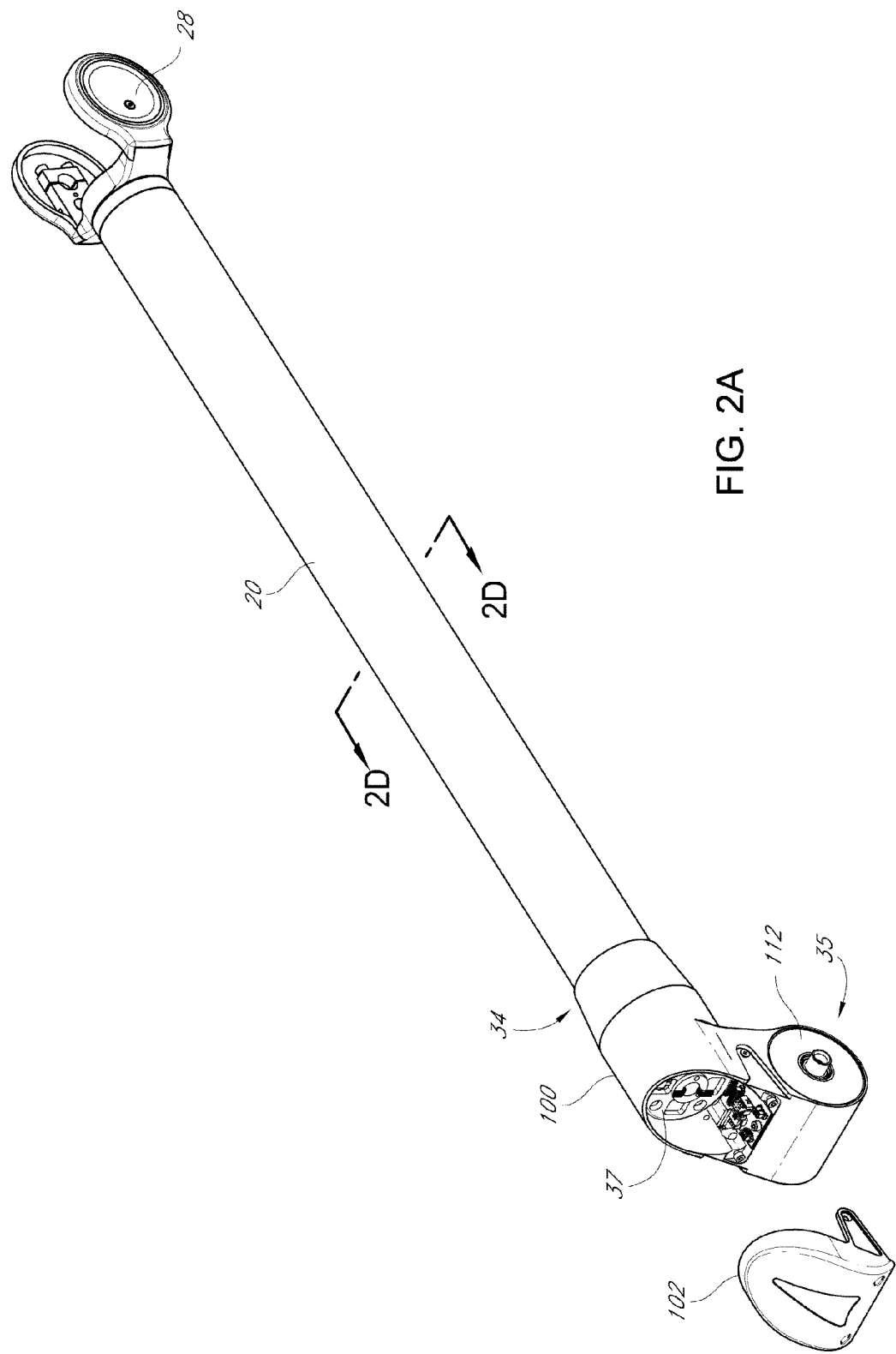
FIG. 2A is a perspective view of the transfer member of FIG. 2 with a cover portion removed.
Figure 2B:
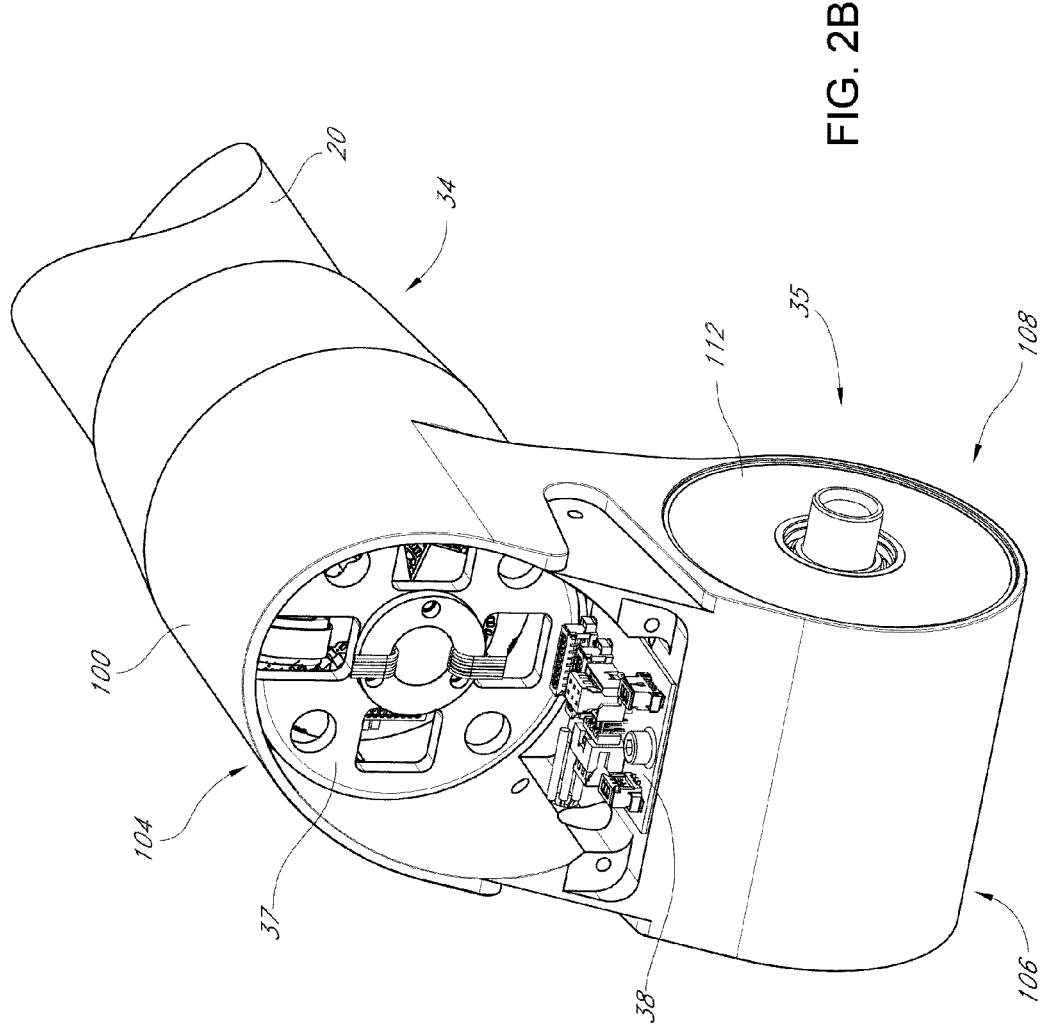
FIG. 2B is an enlarged perspective view of the transfer member of FIG. 2A.
Figure 2D:
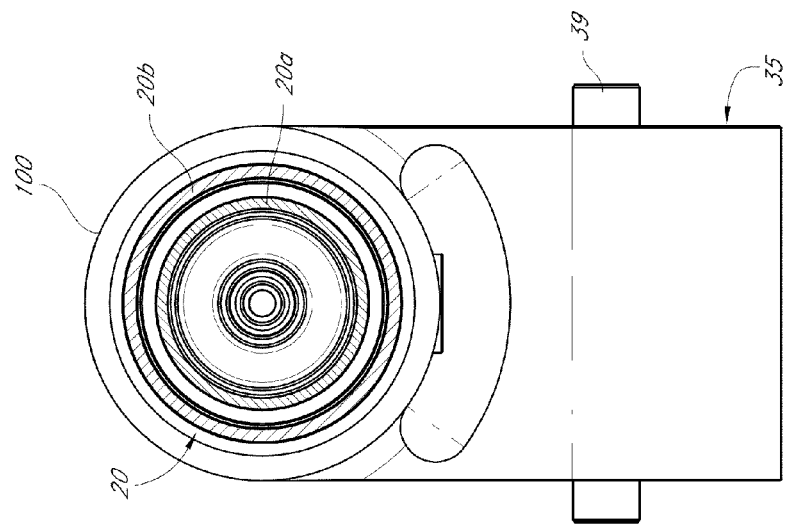
FIG. 2D is an enlarged cross-sectional view of the transfer member of FIG. 2B.
Figure 2C:
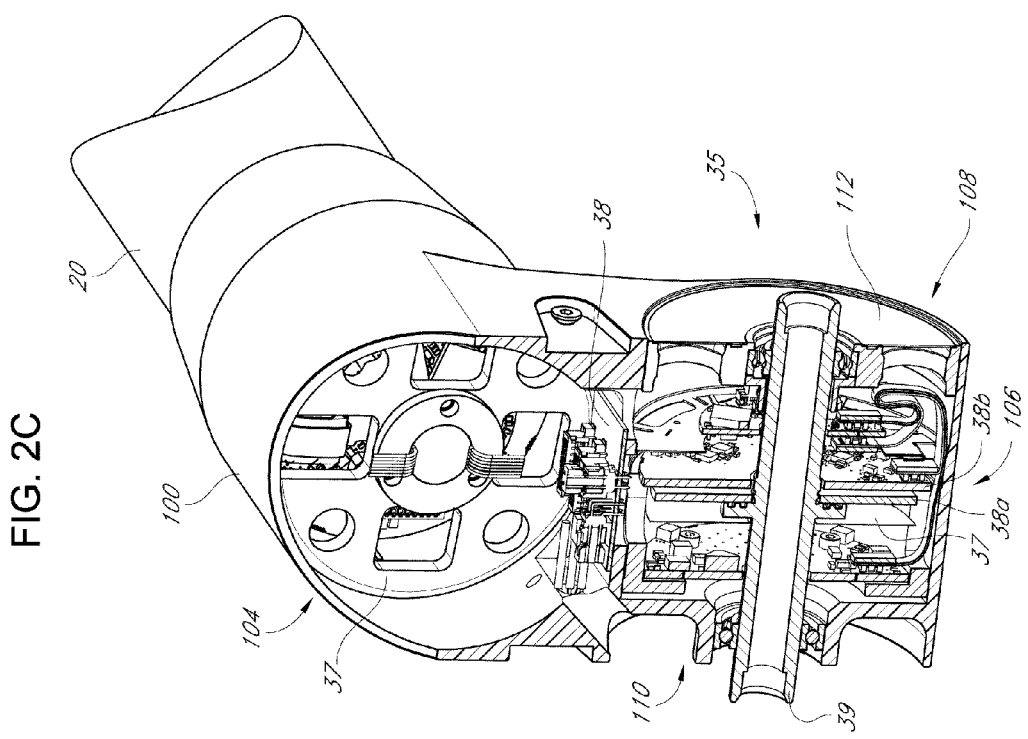
FIG. 2C is an enlarged cross-sectional view of the articulation members of FIG. 2

Each hinge or swiveling joint has its own dedicated motion transducer in the form of an encoder 37 which can be seen in FIG. 2C. Advantageously, both the hinge and swiveling joint encoders are positioned at least partially, and more preferably, entirely within the dual axis housing 100 within the respective articulation members 30-36.

In various embodiments, the coordinate acquisition member 50 includes a contact sensitive member 55 (depicted as a hard probe in FIG. 1) configured to engage the surfaces of a selected object and generate coordinate data on the basis of probe contact. In the illustrated embodiment, the coordinate acquisition member 50 also includes a non-contact scanning and detection component that does not necessarily require direct contact with the selected object to acquire geometry data. As depicted, the non-contact scanning device includes a non-contact coordinate detection device (shown as a laser coordinate detection device/laser scanner) that may be used to obtain geometry data without direct object contact. The non-contact scanning device can include a camera or other optical device 70, which functions in conjunction with a laser not depicted herein. It will be appreciated that various coordinate acquisition member configurations are possible, including: a contact-sensitive probe, a non-contact scanning device, a laser-scanning device, a probe that uses a strain gauge for contact detection, a probe that uses a pressure sensor for contact detection, a device that uses an infrared beam for positioning, and a probe configured to be electrostatically-responsive may be used for the purposes of coordinate acquisition. Further, in some embodiments, a coordinate acquisition member 50 can include one, two, three, or more than three coordinate acquisition mechanisms.

Further description of certain embodiments of a coordinate acquisition member that can be used with the embodiments described herein can be found in U.S. patent application Ser. No. 12/487,535, filed 18 Jun. 2009 and entitled ARTICULATING MEASURING ARM WITH LASER SCANNER, which is incorporated by reference herein in its entirety. As depicted in said reference, the coordinate acquisition member can include a modular laser scanner that can attach to the main body of the coordinate acquisition member (which can also include a touch probe). The modular features can allow various other coordinate detection devices to be used with the coordinate acquisition member. Additionally, other coordinate acquisition members can be used, as is generally known by those of skill in the art.

Advantageously, as depicted in FIGS. 2-2C, the articulation members 30-36 can form a dual-axis housing 100. The dual-axis housing 100 can be a single monoblock housing or a housing comprising multiple pieces bonded together (e.g. by welding, adhesive, etc.). As depicted, the dual-axis housing 100 can be coupled to the transfer members 20 and include part of the hinge and swivel joints, corresponding to the second and third axes of rotation from the base 10. As noted above, separately functional rotational encoders 37 and associated electronics for measuring a position of the transfer members and hinge and swivel joints (as are generally known by those of skill in the art) can be positioned in the articulation members 34 and 35 (as well as the articulation members 30-33 and 36, depicted in other figures).

To facilitate assembly of the dual-axis assembly, the dual-axis housing 100 can include a removable back cover 102, shown removed in FIG. 2A. As depicted, the removable cover 102 can cover an opening in the housing 100 generally axially aligned with an adjacent transfer member 20 mounted to the housing. Further, in some embodiments the cover 102 can be configured so as not to bare any significant load of the CMM 1. Accordingly, it may be desirable to form the cover 102 of a less rigid material that can also serve as a shock absorber. As depicted, the cover 102 can be positioned at an "elbow" position of the arm 1. During some activities, the "elbow" positions may be more likely to abruptly contact an external, hard surface that could damage the arm 1. Advantageously, a cover 102 formed of a shock absorbent material can protect the arm 1 from such damage. Even further, in some embodiments, the material of the cover 102 can also serve to promote enhanced sealing with the material of the dual-axis housing 100. The dual-axis housing 100 can include a rigid material, and the cover 102 can include a more flexible material that can conform to the edges of the housing when mounted thereto, creating an enhanced seal.

Figure 2E:
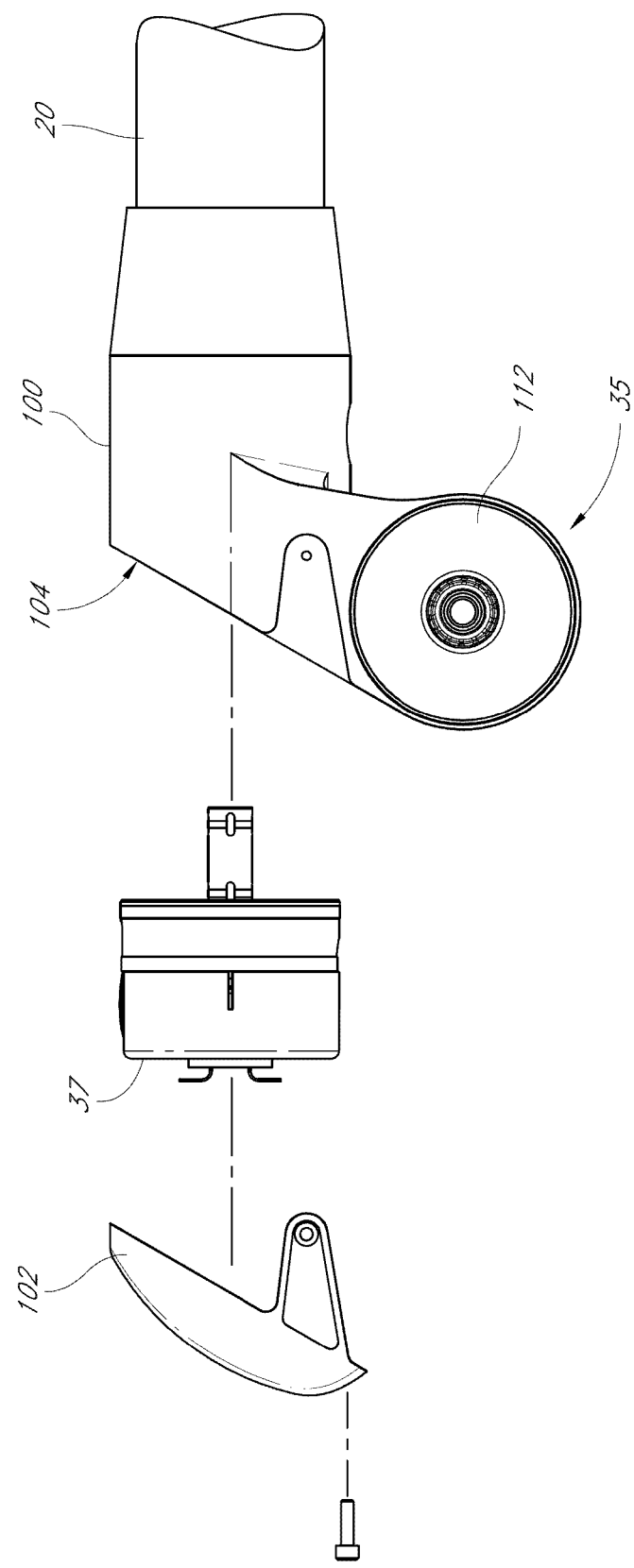
FIG. 2E is a partially exploded side view of the transfer member and articulation members of FIG. 2.

The removable back cover 102 can provide a general sealing of the interior of the dual-axis housing 100 from the external elements, protecting the encoders 37 positioned within the housing. When the cover 102 is removed the separate encoder 37 associated with the articulation member 34 can be exposed and inserted/removed from the dual-axis housing 100 into a swivel-receiving portion 104 generally axially aligned with the depicted transfer member 20 (as depicted in FIG. 2E). In the illustrated embodiment, the encoders associated with the articulation members 34 and 35 are separate components from the transfer members 20. That is, the encoder and transfer member are two separate and distinct components that are connected together but can rotatably operate apart from each other. The same principle can also be applied to the other articulation members 30-33 and 36. That is, the transfer members 20 can operate separately from the articulation members 30-36 that form a joint or joint assembly as described above and operate to measure rotation.

Additionally, additional electronics can be inserted/removed while the cover 102 is removed, as depicted in FIG. 2B. As shown, the dual-axis housing 100 can provide a receiving portion for a printed circuit board 38 that can hold additional electronics. In some embodiments, the additional electronics can perform additional signal processing such as digitizing an analog signal from the encoders. In some embodiments, such digitization can be performed prior to passing the signal to slip rings or other rotatable electronic connections. Further, in some embodiments the additional printed circuit board 38 can facilitate forming the physical electronic connection between both encoders within the dual-axis housing 100.

Further, in the depicted dual-axis housing 100 the separate encoder 37 associated with the articulation member 35 can be inserted/removed independent of the back cover 102. To facilitate this insertion/removal, the dual-axis housing 100 can have a hinge-receiving portion 106 oriented perpendicularly from a primary plane of the housing. The hinge-receiving portion 106 can have an open end 108, into which the encoder 37 can enter, and a substantially closed end 110 against which the encoder can abut to define a position for the encoder. Once the encoder 37 has been inserted, a cap piece 112 can then be inserted to secure the encoder within the hinge-receiving portion 106.

As depicted in FIG. 2C, the encoder 37 can include an encoder disk 38a and a read head 38b. The encoder disk 38a can have a pattern on its surface that can be measured by the read head 38b. For example, in some embodiments the encoder disk 38a can have an optical pattern including varying colors, transparent and opaque portions, or other visible variations; and the read head 38b can include an optical measuring device such as a camera. In some embodiments the disk 38a can have a defined pattern of lines on the disk similar to a bar code such that any image of the disk by the read head can define an absolute rotational angle, as further discussed below. As another example, the encoder disk 38a can have varying magnetic portions and the read head 38b can measure a corresponding magnetic field. The varying patterns on the encoder disk 38a can be measured by the read head 38b to indicate a rotational position, or a change in rotational position of the encoder disk relative to the read head. In turn, as depicted, the read head 38b can be rotationally fixed with the housing 100 and the encoder disk 38a can be rotationally fixed to an encoder shaft 39 that is rotatably mounted within the housing. Thus, rotation of the shaft 39 relative to the housing 100 can cause a corresponding relative rotation between the disk 38a and read head 38b that can be measured. However, it will be clear from the description herein that the apparatus can vary. For example, in some embodiments the read head 38b can be rotatably mounted to the housing 100 and the encoder disk 38a can be rotatably fixed.

In the depicted embodiment, the encoder associated with the articulation member 35 can mount with an adjacent transfer member, not shown in FIG. 2, via a fork joint on the transfer member and the encoder shaft 39. Said fork joint can be similar to that depicted at the end of the depicted transfer member 20 opposite the dual-axis housing 100, with a yoke 28 that can mount to the encoder shaft 39 rotatably mounted within the housing 100. The forks of the yoke 28 can mount about the ends of the dual-axis housing 100 and its contained encoder to form a hinge articulation member 35. Accordingly, both encoders in the dual-axis housing 100 can be inserted/removed independently of one another from the single housing. Notably, in other embodiments the form of the dual-axis housing 100 can vary. For example, in some embodiments the dual-axis housing 100 can form two swivel-receiving portions 104, or two hinge-receiving portions 106, as opposed to one of each.

Placing the encoders 37 into a single housing can provide numerous advantages over prior art assemblies with separate housings. For example, the combined housing can reduce the number of parts and joints required, and thus also reduce cost and assembly time. Further, the accuracy of the device can improve from the elimination of deflection, misalignment, or other problems with multiple components. Additionally, removal of the additional housing can allow a more compact combined joint assembly, allowing the arm to be better supported and have less weight. As shown FIG. 1A, a yoke 28 of the next or proceeding transfer member 20 can be coupled to the bearing shaft extending through dual axis housing 100 to form the hinge joint.

Although depicted as enclosing the second and third axes from the base, a similar dual-axis housing 100 can be used with other combinations of articulation members, such as the fourth and fifth articulation members 32, 33. Further, the dual-axis housing can provide additional advantages not explicitly discussed herein. However, it should be noted that in other embodiments of the inventions described herein, the articulation members 30-36 can each have a separate housing.

It should be appreciated that the dual-axis housing or joint assembly described above can be used in other types of CMMs and need not be used in combination with the additional embodiments described below.

Figure 3:
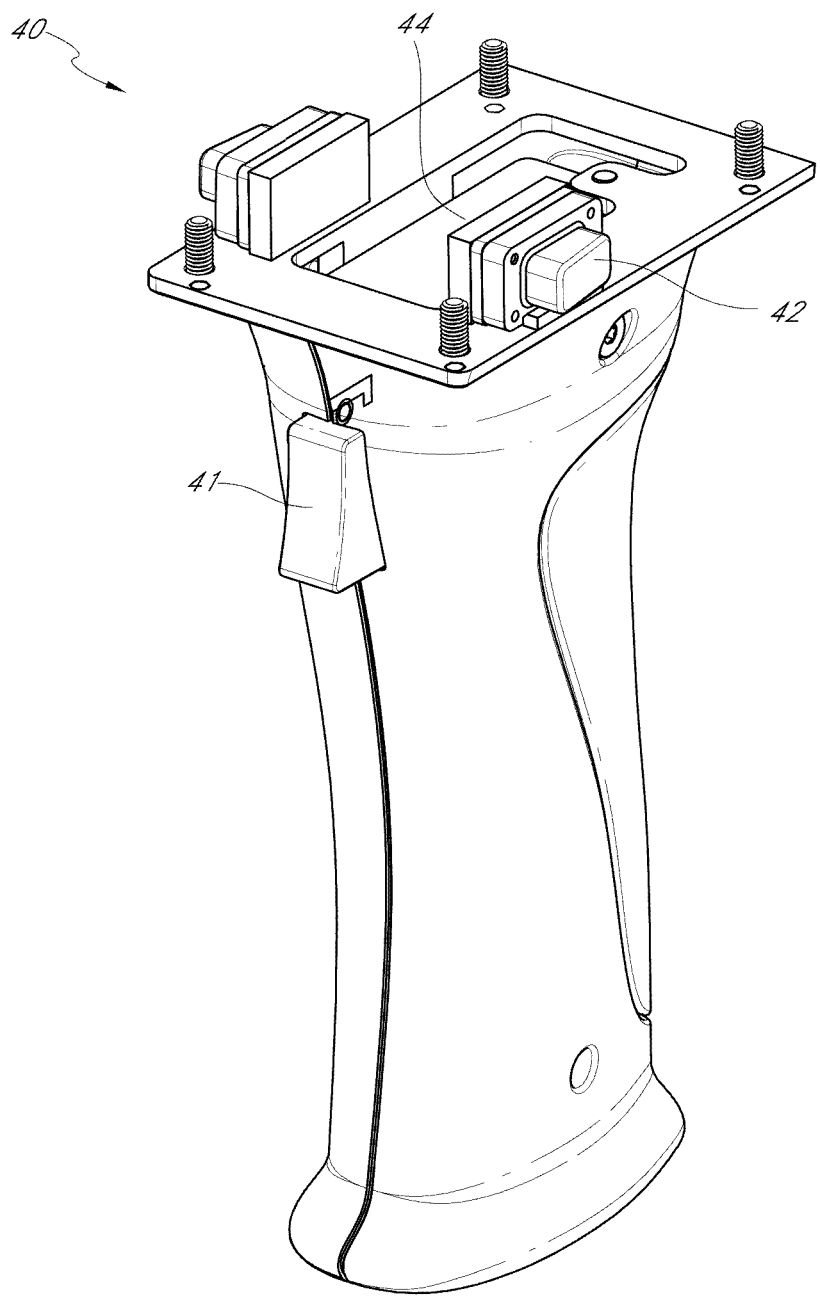
FIG. 3 is a perspective view of a handle of the articulated arm of FIG. 1.

FIG. 3 depicts an improved handle 40. The handle 40 can include one or more integrated buttons 41. The handle can connect to the axis with bolts, snaps, or clamps. Additionally, the handle 40 can include electronics 44 included within its interior. Advantageously, providing the electronics 44 in the handle 40 can further separate the electronics from rotational encoders and other components that may lose accuracy when heated. In some embodiments the handle 40, or the electronics 44 therein, can be thermally isolated from the remainder of the arm. Additionally, when the handle 40 is removable and includes the electronics 44, it can form a modular component similar to the feature packs (described below). Thus, a user can change the functionality by changing the handle 40, and accordingly also changing the electronics 44 and the buttons 41 that control the electronics. A plurality of handles 40 with different functionalities can thus be provided in a CMM system to provide modular features to the CMM. Again, it should be noted that in other embodiments of the inventions described herein, a different handle can be used, or alternatively there can be no distinct handle. Additionally, the handle can contain a battery to power the arm, the scanner or both.

Figure 6:
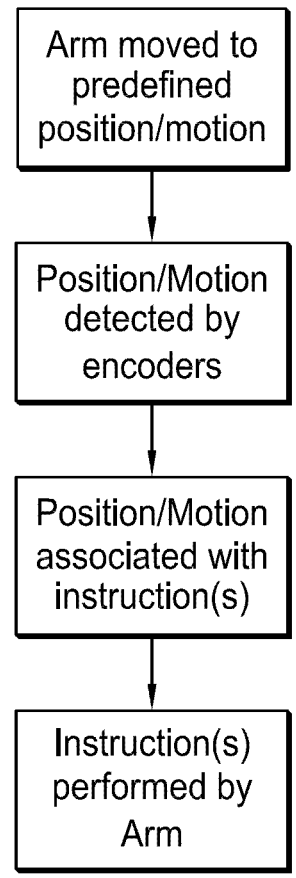
FIG. 6 is a flow diagram of a method of operating an articulated arm.

It should be appreciated the improved handle 40 described above can be used in other types of CMMs and need not be used in combination with the additional embodiments described above and below the preceding section Additionally or alternatively, in some embodiments a CMM arm 1 can be at least partially controlled by motion of the arm itself, as depicted in FIG. 6. For example, whereas some commands or instructions may be triggered by the pressing of a button, pulling a lever, turning a dial, or actuating some other traditional actuation device in some embodiments, in other embodiments the same or different instruction can be triggered by a specific motion or position of the CMM arm 1, which can be detected by the encoders 37. As a more specific example, in some embodiments the CMM arm 1 can be instructed to enter a sleep mode when the arm is placed in a generally folded or retracted position, such as that depicted in FIG. 1. The CMM arm 1 can then perform that instruction. Similarly, the CMM arm 1 can be reawakened by a rapid movement, or movement into a more extended position. Other combinations of instructions, motions, and positions are possible.

For example, in some embodiments the CMM arm 1 can enter into different data acquisition modes depending on its general orientation. Varying the data acquisition mode by position can be advantageous where the CMM arm 1 regularly measures products that require different data acquisition modes along different parts of a product.

Further, in some embodiments the arm can enter into different data acquisition modes depending on its speed of movement. For example, an operator of the CMM may move the CMM slowly when a critical point will soon be measured. Thus, the CMM can increase its measurement frequency, accuracy, or other characteristics when the arm is moving slowly. Additionally, the CMM can be toggled between a mode where the arm is used as a computer mouse and a measurement mode with a quick movement of one of the last axes (embodiments of an associated computer further described below).

As with the previous embodiments, it should be appreciated that these features related to control of the arm can be used in other types of CMMs and need not be used in combination with the additional embodiments described above and below the preceding section.

Figure 4:
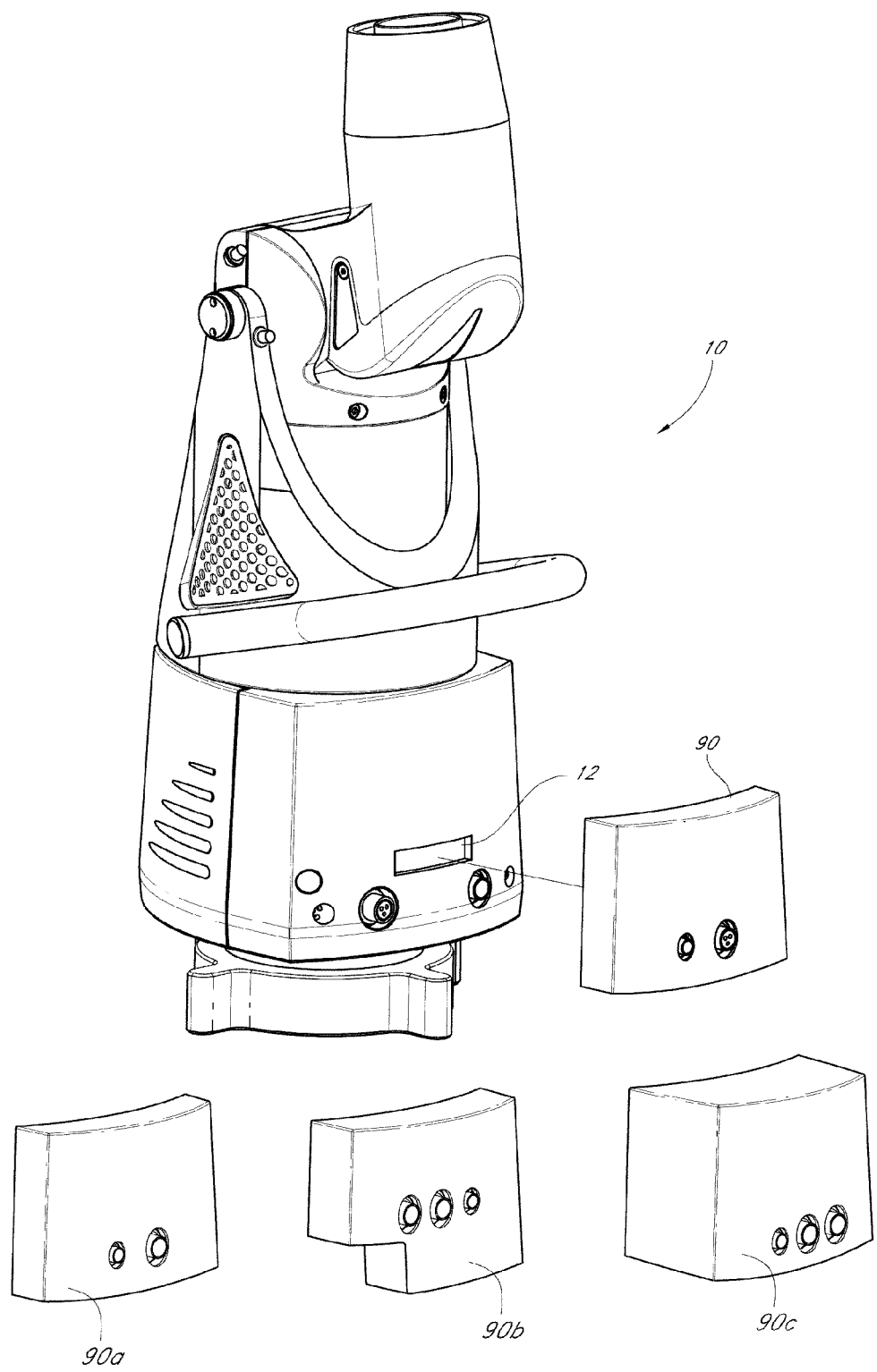
FIG. 4 is a perspective view of a base and a feature pack of the articulated arm of FIG. 1.

FIG. 4 depicts a set of feature packs 90 that can connect with the base 10 via a docking portion 12. The docking portion 12 can form an electronic connection between the CMM arm 1 and the feature pack 90. In some embodiments the docking portion 12 can provide connectivity for high-speed data transfer, power transmission, mechanical support, and the like. Thus, when connected to a docking portion, a feature pack 90 can provide a modular electronic, mechanical, or thermal component to the CMM arm 1, allowing a variety of different features and functionality such as increased battery life, wireless capability, data storage, improved data processing, processing of scanner data signals, temperature control, mechanical support or ballast, or other features. In some embodiments this modular functionality can complement or replace some modular features of the handle 40. The modular feature packs can contain connectors for enhanced functionality, batteries, electronic circuit boards, switches, buttons, lights, wireless or wired communication electronics, speakers, microphones, or any other type of extended functionality that might not be included on a base level product. Further, in some embodiments the feature packs 90 can be positioned at different portions of the CMM arm 1, such as along a transfer member, an articulation member, or as an add-on to the handle 40.

As one example, a feature pack 90 can include a battery, such as a primary battery or an auxiliary battery. Advantageously, in embodiments where the pack 90 is an auxiliary battery the CMM can include an internal, primary battery that can sustain operation of the CMM while the auxiliary battery is absent or being replaced. Thus, by circulating auxiliary batteries a CMM can be sustained indefinitely with no direct power connection.

As another example, a feature pack 90 can include a data storage device. The available data storage on the feature pack 90 can be arbitrarily large, such that the CMM can measure and retain a large amount of data without requiring a connection to a larger and/or less convenient data storage device such as a desktop computer. Further, in some embodiments the data storage device can transfer data to the arm, including instructions for arm operation such as a path of movement for a motorized arm, new commands for the arm upon pressing of particular buttons or upon particular motions or positions of the arm, or other customizable settings.

In examples where the feature pack includes wireless capability, similar functionality can be provided as with a data storage device. With wireless capability, data can be transferred between the CMM and an external device, such as a desktop computer, continuously without a wired connection. In some embodiments, the CMM can continuously receive commands from the auxiliary device. Further, in some embodiments the auxiliary device can continuously display data from the arm, such as the arm's position or data points that have been acquired. In some embodiments the device can be a personal computer ("PC") and the feature pack can transmit arm coordinate data and scanner data wirelessly to the PC. Said feature pack can combine the arm data and scanner data in the feature pack before wireless transmission or transmit them as separate data streams.

In further embodiments, the feature packs can also include data processing devices. These can advantageously perform various operations that can improve the operation of the arm, data storage, or other functionalities. For example, in some embodiments commands to the arm based on arm position can be processed through the feature pack. In additional embodiments, the feature pack can compress data from the arm prior to storage or transmission.

In another example, the feature pack can also provide mechanical support to the CMM. For example, the feature pack can connect to the base 10 and have a substantial weight, thus stabilizing the CMM. In other embodiments, the feature pack may provide for a mechanical connection between the CMM and a support on which the CMM is mounted.

In yet another example, the feature pack can include thermal functionality. For example, the feature pack can include a heat sink, cooling fans, or the like. A connection between the docking portion and the feature pack can also connect by thermally conductive members to electronics in the base 10 and the remainder of the CMM, allowing substantial heat transfer between the CMM arm and the feature pack.

Further, as depicted in FIG. 1, in some embodiments the feature packs 90 can have a size and shape substantially matching a side of the base 10 to which they connect. Thus, the feature pack 90 can be used without substantially increasing the size of the CMM, reducing its possible portability, or limiting its location relative to other devices.

Again, the feature packs 90 can be used in combination with each other and the other features described herein and/or can be used independently in other types of CMMs.

Figure 5:
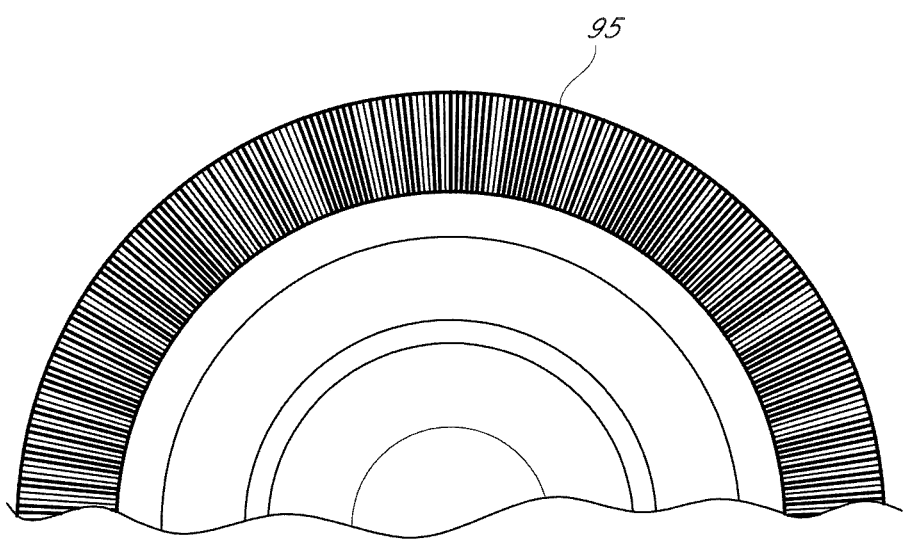
FIG. 5 is a plan view of a demonstrative embodiment of an encoder.

Additionally, in some embodiments the CMM arm 1 can include an absolute encoder disk 95, a demonstrative embodiment depicted in FIG. 5. The absolute encoder disk 95 can include a generally circular, serialized pattern that can be embodied in reflective and non-reflective materials, translucent and non-translucent materials, alternating magnetic properties, or the like. The serialized pattern can allow a read head to determine a unique position on the encoder by only reading a limited portion of the encoder's coded surface. In some embodiments, the serialized pattern can resemble a bar code, as depicted in FIG. 5. The pattern can be non-repetitive along a viewing range of an associated read-head. Thus, an image or other data collected by the read-head from the encoder disk 95 can yield a pattern unique from any other position on the encoder, and therefore be associated with a unique angular position. Each encoder can consist of a single serialized disk that is read by one or more read-heads that can be, e.g., CCD imagers. The use of two or preferably four CCD imagers can improve the accuracy of the encoder by measuring the eccentricity of the axis and subtracting out the eccentricity from the angle measurement. Further, the angle accuracy can be improved by averaging the measurements of the multiple CCD imagers.

In prior art encoders an incremental and repetitive surface was often used, in which the coded surface only indicates incremental steps and not an absolute position. Thus, incremental encoders would require a return to a uniquely identified home position to re-index and determine the incremental positions away from the home position. Advantageously, some embodiments of an absolute encoder disk 95 can eliminate the required return to a home position. This feature of a CMM can also be used in combination with the other features described herein and/or can be used independently in other types of CMMs.

Advantageously, the absolute encoder disk 95 can improve functionality of a CMM arm 1 that enters a sleep mode. Entering sleep mode can reduce the power consumption of a CMM arm 1. However, if enough systems are shut down during sleep mode then incremental encoders may "forget" their position. Thus, upon exiting sleep mode incremental encoders may need to be brought back to the home position prior to use. Alternatively, incremental encoders can be kept partially powered-on during sleep mode to maintain their incremental position. Advantageously, with an absolute encoder disk 95 the encoders can be completely powered off during sleep mode and instantly output their position when power is returned. In other modes, the absolute encoder can read its position at a lower frequency without concern that it may miss an incremental movement and thus lose track of its incremental position. Thus, the CMM arm 1 can be powered-on or awakened and can immediately begin data acquisition, from any starting position, without requiring an intermediary resetting to the "home" position. In some embodiments absolute encoders can be used with every measured axis of rotation of the CMM. This feature of a CMM can also be used in combination with the other features described herein and/or can be used independently in other types of CMMs. For example, as described above, this sleep mode can be induced by movement into a particular position. As a further example, the encoder disk 38a can be an absolute encoder disk 95.

Even further, in some embodiments the CMM arm 1 can include a tilt sensor. In some embodiments the tilt sensor can have an accuracy of at least approximately 1 arc-second. The tilt sensor can be included in the base 10, a feature pack 90, or in other parts of the CMM arm 1. When placed in the base 10 or the feature pack 90, the tilt sensor can detect movement of the CMM arm's support structure, such as a table or tripod on which the arm sits. This data can then be transferred to processing modules elsewhere in the arm or to an external device such as a computer. The CMM arm 1 or the external device can then warn the user of the movement in the base and/or attempt to compensate for the movement, for example when the tilt changes beyond a threshold amount. Warnings to the user can come in a variety of forms, such as sounds, LED lights on the handle 40 or generally near the end of the arm 1, or on a monitor connected to the arm 1. Alternatively or additionally, the warning can be in the form of a flag on the data collected by the arm 1 when tilting has occurred. This data can then be considered less accurate when analyzed later. When attempting to compensate for the movement, in some embodiments the tilting and its effects on position can be partially measured and accounted for in the calibration process. In further embodiments, the tilting can be compensated by adjusting the angular positions of the articulation members accordingly. This feature of a CMM can also be used in combination with the other features described herein and/or can be used independently in other types of CMMs.

In further embodiments, a trigger signal is sent from the arm to the scanner upon each measurement of the arm position. Coincident with the arm trigger the arm can latch the arm position and orientation. The scanner can also record the time of receipt of the signal (e.g. as a time stamp), relative to the stream of scanner images being captured (also, e.g., recorded as a time stamp). This time signal data from the arm can be included with the image data. Dependent on the relative frequency of the two systems (arm and scanner) there may be more than one arm trigger signal per scanner image. It might not be desirable to have the arm running at a lower frequency than the scanner, and this usually results in the arm and scanner frequencies being at least partially non-synchronized. Post-processing of the arm and scanner data can thus combine the arm positions by interpolation with the scanner frames to estimate the arm position at the time of a scanner image. In some embodiments, the interpolation can be a simple, linear interpolation between the two adjacent points. However, in other embodiments higher-order polynomial interpolations can be used to account for accelerations, jerks, etc. This feature of a CMM can also be used in combination with the other features described herein and/or can be used independently in other types of CMMs.

CMM with Flaw Detection

Figure 7:
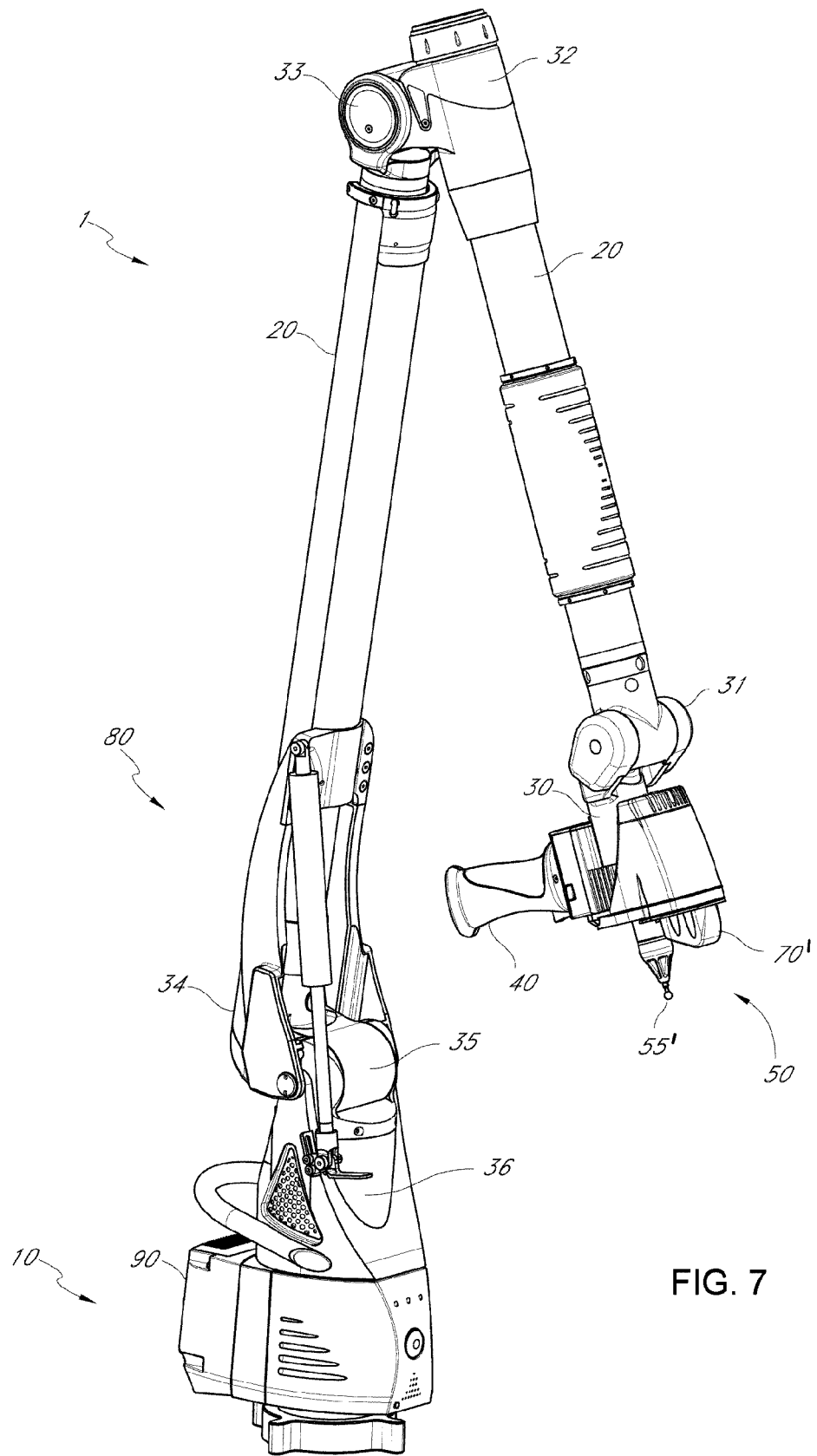
FIG. 7 is a perspective view of one embodiment of a PCMM incorporating an ultrasonic flaw detection system.
Figure 8:
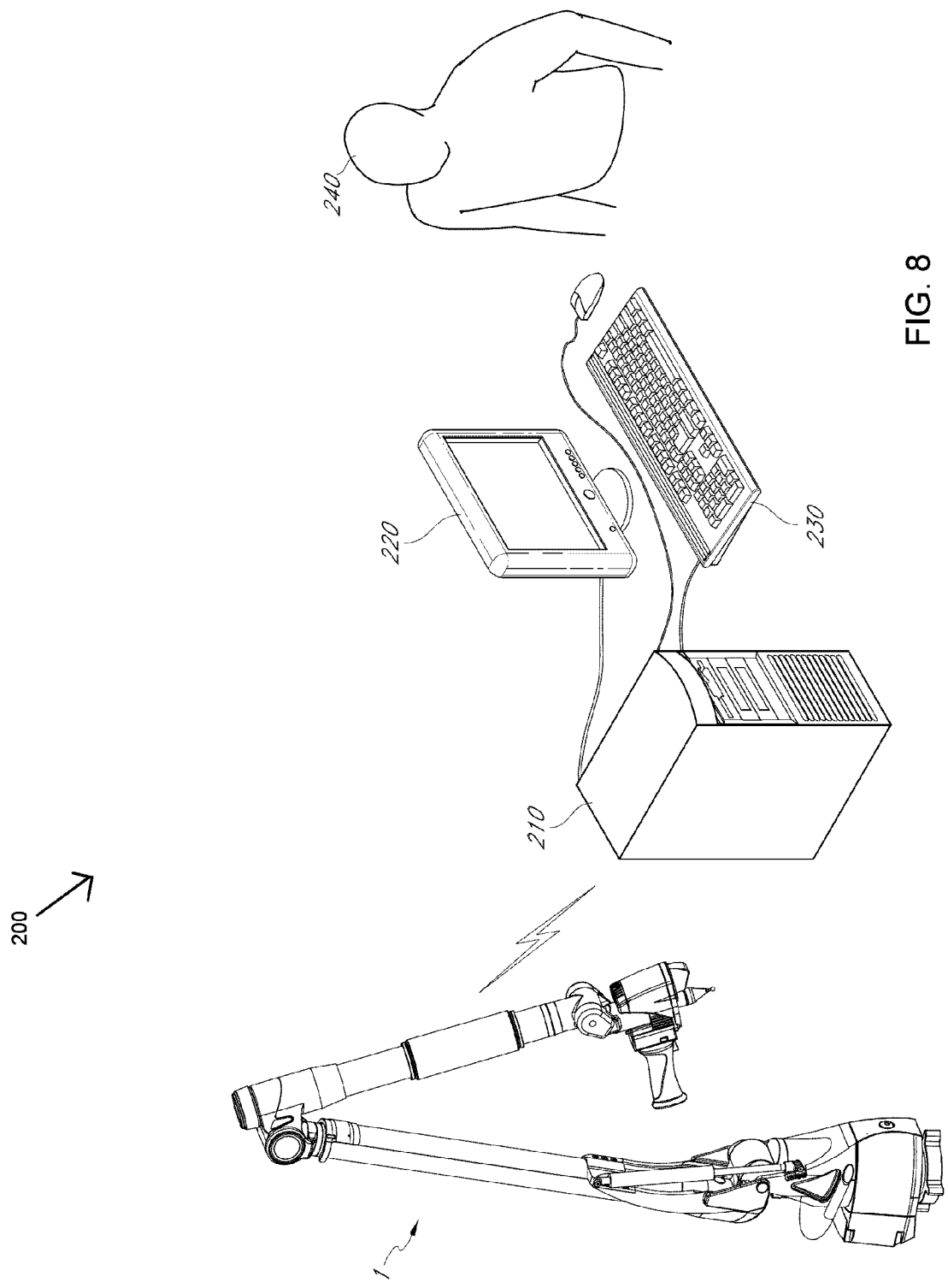
FIG. 8 is a perspective view of one embodiment of an ultrasonic flaw detection system.

FIG. 7 is a perspective view of one embodiment of a PCMM incorporating an ultrasonic flaw detection system. FIG. 8 is a perspective view of one embodiment of an ultrasonic flaw detection system. In further embodiments, the CMM, which may include for example the various embodiments of the PCMM 1 described above, can incorporate a flaw detection system. In some embodiments, that flaw detection system may include an ultrasonic flaw detection system. The ultrasonic flaw detection system 200 can be used in conjunction with any of the embodiments of coordinate measuring machines discussed above as well as any coordinate measuring machines known by those skilled in the art. The ultrasonic flaw detection system 200 can include the CMM (such as the CMM described above) with a flaw detection sensor 55', which can in one arrangement be used in place of the contact sensitive member 55 described above. In some embodiments, the flaw detection sensor 55' may include an ultrasonic flaw detection sensor. The system 200 can also include a computer or processor for processing information from the CMM and the sensor 55'. As will be explained below, combining an ultrasonic flaw detection system with a CMM provides the capability to not only take multiple measurements simultaneously, but the capability to simultaneously display those results (e.g., on a computer display 220). In some embodiments, the data from the ultrasonic flaw detection system 200 may be overlaid with the data from the coordinate measuring machine. The data from the coordinate measuring machine in conjunction with the data simultaneously or substantially simultaneously provided by the ultrasonic flaw detection system can be used to reconstruct the visible surface and the hidden surface of the selected object together. In some embodiments, the CMM incorporating an ultrasonic flaw detection system provides the capability to provide a three dimensional color map of flaws in the selected object. In some embodiments, the flaws may be incorporated into a three dimensional model of the selected object. In other embodiments, the flaws may be incorporated into a three dimensional model created using computer assisted drafting software. In some embodiments, the three dimensional color map of the flaws may be incorporated into a three dimensional model of the selected object.

In some embodiments, an ultrasonic flaw detection system has the capability to locate and categorize flaws in selected objects. An ultrasonic flaw detection system can include an ultrasound sensor 55' which may include one or more ultrasonic transducers, hardware, and software for signal capture and analysis, a waveform display, and in some applications, a data logging module. In some embodiments, at least one ultrasonic transducer is utilized to convert energy from one form to another. The transducer can convert electrical energy into high frequency sound energy and vice versa. In some embodiments, the ultrasound sensor includes an ultrasonic pulser and receiver. In one embodiment, the ultrasonic flaw detection system can generate sound waves via mechanical vibration and propagate through a medium (e.g., a selected object to me measured). The waves will travel through a medium at a specific speed or velocity, in a predictable direction, and when they encounter a boundary with a different medium they will be reflected or transmitted according to simple rules. The ultrasonic flaw detection system can detect and measure the reflected waves. In some embodiments, the ultrasonic flaw detection system can include an active element made of a piezoelectric ceramic, composite, or polymer. When the active element is excited by a high voltage electrical pulse, it vibrates across a specific spectrum of frequencies and generates a burst of sound waves. When the active element is vibrated by an incoming sound wave, it generates an electrical pulse. In some embodiments, a thin layer of coupling liquid or gel is utilized between the transducer and the selected object as sound energy at ultrasonic frequencies typically does not travel efficiently through gasses.

Several types of ultrasonic transducers can be used in various embodiments of the ultrasonic flaw detection system described herein. These transducers may include, for example, contact transducers, angle beam transducers, delay line transducers, immersion transducers, and dual element transducers. The embodiments described herein can incorporate at least one of each of these types of ultrasonic transducers. In some embodiments, a variety of ultrasonic transducers can be included.

In some embodiments, an ultrasonic flaw detector may utilize straight beam testing or angle beam testing. Straight beam testing utilizing contact, delay line, dual element, or immersion transducers may be employed to find cracks or delamination parallel to the surface of the selected object, as well as voids and porosity. The testing can utilize the principle that sound energy travelling through a medium will continue to propagate until it either disperses or reflects off a boundary with another material, such as the air surrounding a far wall or found inside a crack. In this type of test, the operator couples the transducer to the selected object and locates the echo returning from the far wall of the selected object, and then looks for any echoes that arrive ahead of that backwall echo, discounting grain scatter noise if present. An acoustically significant echo that precedes the backwall echo implies the presence of a laminar crack or void. Through further analysis, the depth, size, and shape of the structure producing the reflection can be determined. Angle beam testing utilizing common angle beam (wedge) transducer assemblies or immersion transducers aligned so as to direct sound energy into the selected object at a selected angle, may be employed to find cracks or other discontinuities perpendicular to the selected object. In some embodiments, angle beam assemblies make use of mode conversion and Snell's Law to generate a shear wave at a selected angle in the selected object. As the angle of incident longitudinal wave with respect to a surface increases, an increasing portion of the sound energy is converted to a shear wave in the second material, and if the angle is high enough, all of the energy in the second material will be in the form of shear waves.

As shown in FIG. 7 the coordinate acquisition member 50 of the PCMM 1 may incorporate an ultrasound sensor 55' of an ultrasonic flaw detection system. The ultrasound sensor 55' may incorporate at least one ultrasonic transducer such that the ultrasound sensor 55' is capable of transmitting and receiving ultrasonic sound waves through the selected object and detecting flaws beneath the surface of the selected object as well as the thickness of the measured portion of the selected object. Flaws may include for example, cracks, delamination, porosity, or other defects beneath the surface of the selected object. In one embodiment, the ultrasound sensor 55' may serve as a contact sensitive member configured to engage surfaces of a selected object and generate coordinate data. In some embodiments, the ultrasound sensor 55' incorporates a hard point to engage surfaces of a selected object. By incorporating the ultrasound sensor 55' and the coordinate measurement probe, the CMM can simultaneously or substantially simultaneously collect coordinate data as well as ultrasonic flaw measurement data at the same location. The ultrasonic flaw measurements correlated with the coordinate measurements offers significantly improved information, providing the ability to determine the location of flaws relative to the surface of the selected object and the ultimate location of flaws within the object. In addition, the data collected from multiple locations can be compiled, creating a map of the flaws within the selected object.

In another embodiment, the coordinate acquisition member 50 of the PCMM 1 may optionally incorporate an ultrasound sensor 55' as well as a non-contact scanning and detection component 70' that does not necessarily require direct contact with the selected object to acquire geometry data. The non-contact scanning device 70' may include a non-contact coordinate detection device to obtain geometry data without direct object contact. In one embodiment, the non-contact scanning device 70' may include a laser scanner. In one embodiment, the non-contact scanning device 70' may include an eddy-current device. In one embodiment, the non-contact scanning device 70' may include an X-ray device. In one embodiment, the CMM may utilize a dual mode where the non-contact scanning device 70' and ultrasonic flaw detection system are utilized in turn. In one embodiment, the CMM may first utilize a scan mode where the non-contact scanning device 70' obtains geometry data of the surface of the selected object. Then, the CMM may utilize a flaw detection mode where the ultrasonic flaw detection system measures flaws beneath the surface of the selected object. In some embodiments, the ultrasonic flaw detection system may be utilized to test selected portions, or the entirety of the selected object, during the flaw detection mode. In some embodiments, the order of the two modes may be reversed. In some embodiments, the dual mode procedure may incorporate additional modes for additional data acquisition tools and methods. In some embodiments, each mode may include more than one method or tool for measuring the selected object. In one embodiment, the ultrasonic flaw detection system may be utilized to scan selected portions of interest of the selected object, minimizing the time spent scanning the selected object. This would provide the ability to overlay ultrasonic flaw detection data of the selected portion of interest of the selected object, over a full three dimensional model of the object, providing additional clarity in regards to the location of the flaws.

Figure 9:
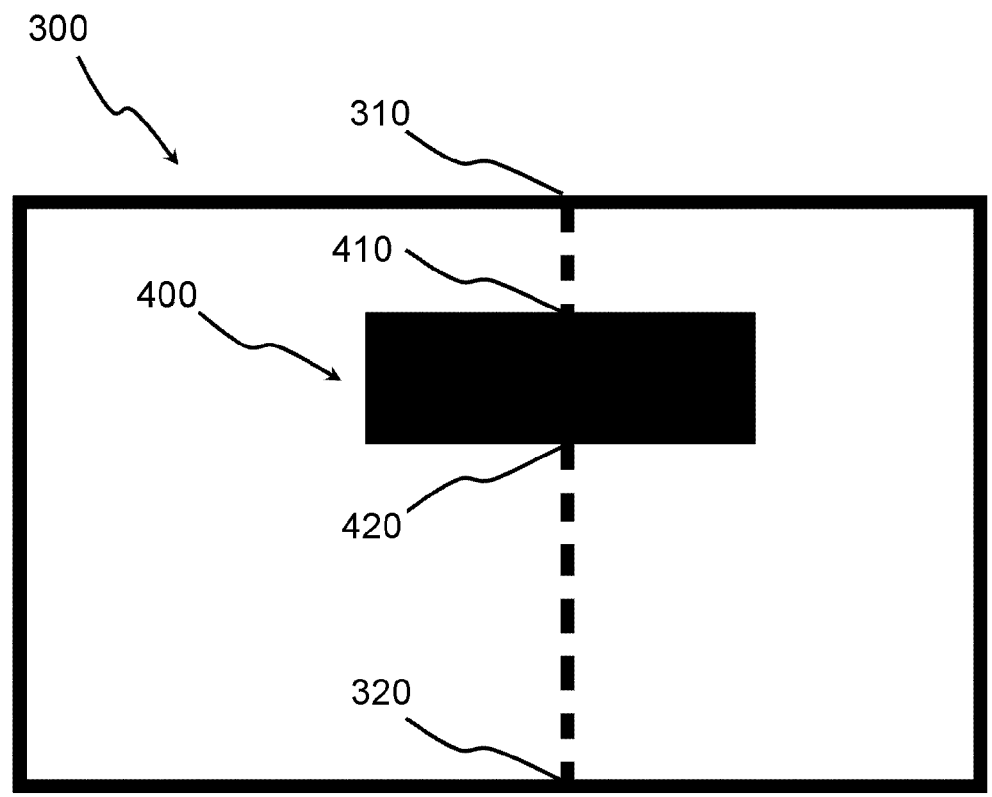
FIG. 9 is a cross section of a selected object including a flaw.

FIG. 9 is a cross section of a selected object 300 including a flaw 400. In one embodiment, the CMM with ultrasonic flaw detection system has the ability to plot two or more points by acquiring a given reading at a given position (given position illustrated by a dotted line in FIG. 9). The two points may include one surface point 310 according to the coordinate measurement provided by the CMM and one flaw point according to the ultrasound flaw detection system of the CMM. In one embodiment, the flaw point may be the closest portion of the flaw to the surface of the selected object 300, or the flaw start point 410. In some embodiments, the CMM with flaw detection system has the ability to plot four or more points by acquiring a given reading at a given position. These points include the surface point 310 and flaw start point 410 as discussed above, in addition to the flaw end point 420 and the opposite surface 320 of the selected object. In one embodiment, in order to obtain the additional points, the ultrasonic flaw detection system may incorporate additional features, which may include for example, the ability to use different frequencies for measuring changes in medium at varying depths. In another embodiment, alternative ultrasonic flaw detection means may be utilized, which may include for example, angled ultrasonic flaw detection. In one embodiment, angled ultrasonic flaw detection may incorporate angled beam transducers. By utilizing angled beam transducers, the ultrasonic flaw detection system can detect and plot the four or more points discussed above. In some embodiments, angled beam transducers may be used in conjunction with the contact transducers to detect and plot the four or more points discussed above. In some embodiments, the ultrasonic flaw detection system will be able to provide the depth of each point discussed above. Therefore, in some embodiments, the system will provide data on the depth or distance between the surface point 310 and the flaw start point 410. In some embodiments, the system will provide data on the thickness of the flaw 400 or the distance between the flaw start point 410 and the flaw end point 420. In some embodiments, the system will provide data on the distance from the flaw end point 420 to the opposite surface 320 of the selected object 300. In some embodiments, the system will be capable of measuring multiple flaws of different depths at a given location. In some embodiments, the system may provide data on the flaw start point 410 and flaw end point 420 of each flaw 400. In some embodiments, the system may provide the thickness at a given position of the selected object 300 or the distance between the surface 310 and the opposite surface 320.

In some embodiments, the ultrasonic flaw detection system may include an electronics module. In one embodiment, the electronics module communicates with the ultrasound sensor 55'. In some embodiments, the electronics module produces and receives the analog signal utilized by the ultrasound sensor 55' to detect flaws beneath the surface of the selected object. In some embodiments, the electronics module also processes the analog signal and produces a digital signal. In some embodiments, the electronics module communicates with other portions of the ultrasonic flaw detection system. In some embodiments, the electronics module may communicate with a hub. In some embodiments, the electronics module may communicate with a feature pack 90 (see FIG. 4). In some embodiments, the electronics module may communicate with an auxiliary device, which may include for example, a computer 210 (See FIG. 8).

In one embodiment, the electronics module is located in close proximity to the ultrasound sensor 55'. In one embodiment, the electronics module is mounted on or within the coordinate acquisition member 50 of the PCMM 1. An advantage of placing the electronic module within the coordinate acquisition member 50 is that it is possible to digitize the ultrasound signal close to the transducer. By digitizing the ultrasound signal close to the transducer, it is possible to transmit a digitized signal through the internal wiring of the PCMM which has slip rings at its joints to provide infinite rotation. If the signal was not digitized close to the coordinate acquisition member then the analog ultrasound signal would need to be transmitted along a separate cable on the outside of the PCMM which would prevent infinite rotation of the PCMM and would be awkward for the user as it could contact the part being measured. Transmitting the raw analog signal through the internal cabling and through the slip rings is not advantageous as it could corrupt a raw analog signal and make it noisy. In some embodiments, the electronics module communicates with the ultrasound sensor 55' via at least one cable. In some embodiments, instead of a cable, the ultrasonic flaw detection system may utilize wireless technology for communication between portions of the system and with other systems. In some embodiments, the electronics module may be located near the base 10 of the PCMM. In one embodiment, the cables connecting the ultrasound sensor 55' to the electronics module may run along the exterior of the plurality of rigid transfer members 20. In another embodiment, the cables may run within the interior of the plurality of rigid transfer members 20. In one embodiment, the CMM may incorporate attachment members to retain the cables and prevent crimping or crushing of the cables during use of the CMM.

In one embodiment, the CMM may incorporate a user interface, which may include for example, a computer monitor 220 (See FIG. 8), to display the data provided by the CMM. In one embodiment, the user interface may be constructed to display data provided by the ultrasonic flaw detection system. In one embodiment, the user interface may be incorporated in the electronics module of the ultrasonic flaw detection system. In another embodiment, a separate user control device may incorporate the user interface. In some embodiments, the user interface may be incorporated into or displayed on an auxiliary device, which may include for example, a desktop or laptop computer 210. In some embodiments the auxiliary device may be wired to the CMM. In other embodiments, the auxiliary device may communicate with the CMM via a wireless connection.

In one embodiment, the user interface incorporates at least one display to present the data gathered by the CMM to the user. In one embodiment that display may include for example, a computer monitor 220. In one embodiment, at least one display may present a graphical representation of a flaw beneath the surface of the selected object. In one embodiment, that graphical representation may include the depth of the flaw in relation to the surface. In one embodiment, the graphical representation may include the depth the flaw start point and the depth of the flaw end point. In one embodiment, the graphical representation may include the distance from the surface of the selected object to the opposite surface, providing the thickness of the portion of the selected object being measured. In one embodiment, the depths described above may be provided in numerical form. In one embodiment, the flaw may be represented by a contrasting color on the display. In one embodiment, the display may graphically display the flaw 400 overlaid on the selected object 300 as illustrated in FIG. 9. In one embodiment, at least one display may present a color map portraying the flaws beneath the surface of the selected object. In one embodiment, different colors may represent different levels of material density. In one embodiment, different colors may represent different kinds of flaws, such as porosity, cracks, delamination, etc. In one embodiment, different colors may represent different thickness flaws. In other embodiments, the different colors may represent additional information provided by other complimentary systems and data acquisition devices.

In some embodiments, the ultrasonic flaw detection system may utilize a feature pack 90 for at least a portion of its functionality (See FIG. 4). In one embodiment, the feature pack 90 may provide the functionality of the electronics module described above. In another embodiment, the feature pack 90 may provide the functionality of an auxiliary device. In another embodiment, the feature pack 90 may communicate with the ultrasound sensor 55' through the cables. In one embodiment, the feature pack 90 may be utilized in conjunction with and communicate with an electronics module. In one embodiment, the feature pack 90 may be utilized in conjunction with and communicate with an auxiliary device. In one embodiment, the feature pack 90 may be connected to the ultrasound sensor 55' via at least one cable. In one embodiment, the feature pack 90 may be connected to an auxiliary device via at least one cable. In one embodiment, the feature pack 90 may be connected to the auxiliary device via a wireless connection. In some embodiments, the feature pack 90 may include data processing devices. In one embodiment, the feature pack 90 produces and receives the analog signals necessary to the ultrasound sensor 55' and receives the analog signals from the ultrasound sensor 55' in order to process that signal and provide a digital signal or data regarding flaws beneath the surface of the selected object. In some embodiments, the feature pack 90 may incorporate ultrasonic flaw detection functionality along with other functionalities, which may include for example, the functionalities of the feature pack 90 discussed above, a data storage device, a communication device, etc. In some embodiments, the ultrasonic flaw detection system may include an addition, upgrade, or option to an existing CMM. In some embodiments, the ultrasonic flaw detection system may include a feature pack 90. The feature pack 90 may provide at least a portion of the ultrasonic flaw detection system's functionality and work in conjunction with the ultrasound sensor 55' to provide information regarding flaws beneath the surface of the selected object.

In some embodiments, the CMM is capable of performing multiple measurements at a time. The CMM may utilize a variety of data acquisition devices simultaneously or consecutively. The devices may include for example, hard point and contact sensitive touch probes, non-contact scanning or imaging devices, laser-scanning devices, strain measurements, etc.

In some embodiments, the CMM with ultrasonic flaw detection system is capable of detecting a variety of flaw types in a variety of materials. In one embodiment, the system is capable of detecting and measuring delamination within a composite material, which may include for example, fiberglass or carbon fiber. In one embodiment, the system is capable of detecting and measuring porosity within a casting. In one embodiment, the system is capable of detecting and measuring cracks within a material, which may include for example, ferrous and non-ferrous metals.

In some embodiments, the ultrasonic flaw detection system discussed above may be replaced by an eddy current flaw detection system. In another embodiment, the ultrasonic flaw detection system may work in conjunction with an eddy current flaw detection system. In another embodiment, the ultrasonic flaw detection system may be replaced by an X-ray flaw detection system. In another embodiment, the ultrasonic flaw detection system may work in conjunction with an X-ray flaw detection system. In another embodiment, the CMM may utilize any combination of ultrasonic flaw detection systems, eddy current flaw detection systems, and X-ray flaw detection systems.

The various devices, methods, procedures, and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A flaw detection system comprising:
   a coordinate measuring machine having a base and one or more transfer members, one or more articulation members connecting the one or more transfer members to the base, and a flaw detection sensor at a distal end of the coordinate measuring machine, the coordinate measuring machine being configured to measure a location of the flaw detection sensor;

an electronics module at the distal end of the coordinate measuring machine and configured to generate digitized signals based at least on the ultrasound signal from the flaw detection sensor;

internal cables within the coordinate measuring machine extending from the distal end to the base, the internal cables configured to transmit digitized signals from the flaw detection sensor; and a processor configured to correlate the location of the flaw detection sensor as measured by the coordinate measuring machine with data detected by the flaw detection sensor.

2. The system of claim 1, wherein the processor is integrated with the coordinate measuring machine.

3. The system of claim 1, wherein the processor is integrated with a computer external to the coordinate measuring machine.

4. The system of claim 1, wherein the flaw detection sensor is an ultrasonic flaw detection sensor.

5. The system of claim 1, wherein the flaw detection sensor includes an ultrasonic pulser and receiver.

6. The system of claim 1, wherein flaw detection system is configured to display the results of the CMM and the flaw detection sensor simultaneously.

7. The system of claim 1, wherein flaw detection system is configured to overlay data from the flaw detection sensor with position data from the coordinate measuring machine.

8. The system of claim 1, wherein flaw detection system is configured to display results from the flaw detection sensor as a three dimensional color map.

9. The system of claim 1 further comprising a modular feature pack connected to the coordinate measurement machine and including the electronics module.

10. The system of claim 9, wherein the feature pack forms part of a handle attached at the distal end of the coordinate measuring machine.

11. A method of sensing flaw in an object comprising:
positioning a flaw sensor positioned on a coordinate measuring machine against an object;
sensing a characteristic of the object with the flaw sensor;
generating a digital signal at the flaw sensor based on the sensed characteristic;
measuring the position of the flaw sensor with the coordinate measuring machine; and
correlating the position of the flaw sensor with the sensed characteristic of the object.

12. The method of claim 11, further comprising moving the flaw sensor to a second point, sensing a characteristic of the object with the flaw sensor at the second point, measuring the position of the flaw sensor with the coordinate measuring machine and correlating the position of the flaw sensor at the second point with the sensed characteristic of the object at the second point.

13. A method of sensing flaw in an object comprising:
positioning a flaw sensor positioned on a coordinate measuring machine against the object at a plurality of positions;
sensing a characteristic of the object with the flaw sensor at each of the plurality of positions;
generating a digital signal at the flaw sensor based on the sensed characteristic;
measuring the position of the flaw sensor with the coordinate measuring machine at the plurality of positions where characteristic of the flaw sensor is being sensed; and
correlating the positions of the flaw sensor with the sensed characteristics at the plurality of positions.

14. The method of claim 13, further comprising generating a three dimensional map of the characteristic sensed by the flaw sensor.

15. The method of claim 13, further comprising overlaying the measured positions of the flaw sensors with the characteristic detected by the flaw sensor.

16. A method of measuring data with a coordinate measuring machine comprising:
moving a probe positioned at a distal end of the coordinate measuring machine to a first probe position;
measuring a surface position on an object with a probe;
measuring a flaw point below the surface position with the coordinate measuring machine; and
generating a digital signal indicative of the flaw point at the distal end of the coordinate measuring machine.

17. A method of measuring data with a coordinate measuring machine comprising:
moving a probe positioned at a distal end of the coordinate measuring machine to a plurality of surface positions on an object;
measuring the plurality of surface positions;
measuring a flaw point below each of the plurality of surface positions with the coordinate measuring machine; and
generating a digital signal indicative of the flaw point at the distal end of the coordinate measuring machine.

18. The method of claim 17, further comprising correlating the flaw point with the plurality of surface positions.

19. A method of measuring data with a coordinate measuring machine comprising:
moving a probe positioned at a distal end of the coordinate measuring machine to a plurality of surface positions on an object;
measuring the plurality of surface positions; and
measuring a flaw start point, a flaw end point and a rear surface of the object below each of the surface positions with the probe of the coordinate measuring machine at the first probe position; and
generating a digital signal indicative of the flaw start point, flaw end point, and a rear surface of the object at the distal end of the coordinate measuring machine.

20. The method of claim 19, further comprising correlating the flaw start point, a flaw end point and a rear surface with the surface positions measured by the coordinate measuring machine.

21. A method of measuring data with a coordinate measuring machine comprising:
moving a non contact laser scanner at a distal end of the coordinate measuring machine to a first probe position;
measuring a surface position on an object with a laser scanner;
measuring a flaw point below the surface position with the coordinate measuring machine; and
generating a digital signal indicative of the flaw point at the distal end of the coordinate measuring machine.

22. The method of claim 21 further comprising switching between laser scanning of the surface and flaw detection of the subsurface during measurement.

* * * * *